United States Patent [19]

Tennigkeit et al.

[11] Patent Number: 5,068,102

[45] Date of Patent: Nov. 26, 1991

[54] AGENT FOR THE LONG-LASTING SHAPING OF HAIR

[75] Inventors: Jürgen Tennigkeit, Seeheim; Burkhard Rose, Darmstadt, both of Fed. Rep. of Germany

[73] Assignee: Goldwell AG, Darmstadt, Fed. Rep. of Germany

[21] Appl. No.: 544,743

[22] Filed: Jun. 27, 1990

[30] Foreign Application Priority Data

Jun. 27, 1989 [DE] Fed. Rep. of Germany ....... 3920984

[51] Int. Cl.$^5$ ................................................. A61K 7/09
[52] U.S. Cl. ....................................... 424/72; 424/401
[58] Field of Search ........................................... 424/72

[56] References Cited

U.S. PATENT DOCUMENTS 2,540,494  2/1951  Schwarz ............................... 424/72

FOREIGN PATENT DOCUMENTS 824426  12/1959  United Kingdom .................. 424/72

*Primary Examiner*—Thurman K. Page
*Assistant Examiner*—Susan S. Rucker

[57] ABSTRACT

Agent for the long-lasting shaping of hair, on the basis of a thioglycolic acid ester as reducing agent, preferably of a glycerol monothioglycolic acid ester. The permanent shaping agent contains, in addition to the thioglycolic acid ester, an amount of 2-mercaptopropionic acid monoglycerol ester and/or 3-mercaptopropionic acid monoglycerol ester as shaping agent, and at least one solubilizer.

12 Claims, No Drawings

AGENT FOR THE LONG-LASTING SHAPING OF HAIR

BACKGROUND OF THE INVENTION

The invention relates to an agent for the long-lasting shaping of hair on the basis of a thioglycolic acid ester as reducing agent, preferably of a glycerol monothioglycolic acid ester, as well as the use of the agent for the long-lasting shaping of hair.

In contrast to the mildly alkaline permanent-waving or permanent shaping agents based on thioglycolate which formerly were used exclusively, in recent years permanent shaping agents of a mildly acid to neutral adjustment based on a thioglycolic acid ester have been developed, which cause decidedly less damage to the structure of delicate hair or hair previously damaged by permanent waving or dyeing. To this extent, shaping agents based on a thioglycolic acid ester have proven to be good for the shaping of previously damaged hair. Although these "ester waves" have generally been well tolerated by the persons treated when they are used according to directions, it happens that especially disposed persons become sensitized.

The invention is addressed to the problem of proposing a permanent shaping agent on an ester basis, which in comparison with known permanent shaping agents on the basis of thioglycolic acid esters will display considerably less tendency to sensitize, while having at least equal shaping effectiveness and gentleness on the structure of the hair.

THE INVENTION

Setting out from a shaping agent of the kind described above, this problem is solved in accordance with the invention by the fact that the permanent shaping agent contains, in addition to the thioglycolic acid ester, a content of 2-mercaptopropionic acid monoglycerol ester and/or 3-mercaptopropionic acid monoglycerol ester as shaping agents and at least one solubilizer.

It has been found that, with a content of the 2-mercaptopropionic acid monocglcerol ester and/or of the 3-mercaptopropionic acid monoglycerol ester in the range of 10 to 60% with respect to a permanent shaping agent containing exclusively a thioglycolic acid ester as the active shaping component, a substantial reduction of the sensitizing potential is achieved, an especially preferred range being a content of 20 to 30% of the 2-mercaptopropionic acid monoglycerol ester and/or of the 3-mercaptopropionic acid monoglycerol ester.

The permanent shaping agent in accordance with the invention is applied in a conventional manner by treating the hair with the permanent shaping agent before and/or after it has been brought to the desired shape, e.g., by winding on curlers, then treating it oxidatively to fix the permanent shape, and lastly by drying.

The time the shaping agent is allowed to act can be between 5 minutes to 60 minutes.

In the conventional manner, heat can also be made to act on the hair during the action of the shaping agent, in which case the time of action then ranges between 5 minutes and 40 minutes.

Comparative tests in regard to the waving effect of the shaping agent according to the invention in comparison to the known shaping agents based on a thioglycolic acid ester have shown that the modified shaping agent has at least the same waving effect as the unmodified product—tending even to be slightly stronger—and no greater harm to the hair structure of the shaped hair was observed. This is true both of the modification of the permanent shaping agent with 2-mercaptopropionic acid monoglycerol ester and with 3-mercaptopropionic acid monoglycerol ester or with mixtures of the two esters.

To appraise the sensitizing potential of the new hair shaping agent in comparison to the conventional "acid permanent waves," three formulas A, B and C, differing only in the "reduction phase" were studied under the same conditions with the sensitizing test according to the OECD Guidelines for Testing of Chemicals, Section 4: Number 406, "Skin Sensitization" of 12 May 1981 (corresponding to: Directive 84/449, EEC B.6. "Acute Toxicity—Skin Sensitization") and "Allergic Contact Dermatitis in the Guinea-Pig: Identification of Contact Allergens" Magnusson, B., Kligman, A. M., 1970, published by C. C. Thomas, Springfield, Ill., USA. The reduction phases in these formulas were formed, in the case of A, by commercial glycerol monothioglycolic acid ester (GMTG) approx. 75% solution in glycerol, in the case of B, by 70% commercial GMTG (as in A), 25% 2-mercaptopropionic acid monoglycerol ester approx. 80% solution in glycerol, and 5% solubilizer, while in the case of C, in comparison with formula B, instead of the 2-mercaptopropionic acid monoglycerol ester the same amount of 3-mercaptopropionic acid monoglycerol ester was used. As a result it is found that the modified formulas B and C, in comparison to the conventional formula A, which is to be rated according to the criteria of the tests employed as "moderately sensitizing," resulted in virtually no sensitization.

To sum up, it is found that the modified hair shaping agents have virtually no sensitizing potential, without the need to accept any reduction of the waving effectiveness or greater damage to the hair structure.

Solubilizers that can be used are fatty acid polyethylene glycol esters, nonylphenol polyglycol ethers and other such solubilizers commonly used in cosmetics.

We claim:

1. Agent for the permanent shaping of hair, said agent comprising a mixture of: (a) a thioglycolic acid ester; (b) from 10 to 60% of said thioglycolic acid ester of 2-mercaptopropionic acid monoglycerol ester; and (c) at least one solubilizer.

2. Agent according to claim 1, wherein the thioglycolic ester is glycerol monothioglycollate.

3. Agent according to claim 1, said agent comprising a mixture of; (a) a thioglycolic acid ester; (b) from 20 to 30% of said thioglycolic acid ester of 2-mercaptopropionic acid monoglycerol ester; and (c) at least one solubilizer.

4. Agent according to claim 3, wherein the thioglycolic ester is glycerol monothioglycollate.

5. Agent for the permanent shaping of hair, said agent comprising a mixture of: (a) a thioglycolic acid ester; (b) from 10 to 60% of said thioglycolic acid ester of 3-mercaptopropionic acid monoglycerol ester; and (c) at least one solubilizer.

6. Agent according to claim 5, wherein the thioglycolic ester is glycerol monothioglycollate.

7. Agent according to claim 5, said agent comprising a mixture of (a) a thioglycolic acid ester; said agent (b) from 20 to 30% of said thioglycolic acid ester of 3-mercaptopropionic acid monoglycerol ester; and (c) at least one solubilizer.

8. Agent according to claim 7, wherein the thioglycolic ester is glycerol monothioglycollate.

9. Agent for the permanent shaping of hair, said agent comprising a mixture of (a) a thioglycolic acid ester; (b) from 10 to 60% of said thioglycolic acid ester of a combination of 2-mercaptopropionic acid monoglycerol ester and 3-mercaptopropionic acid monoglycerol ester; and (c) at least one solubilizer.

10. Agent according to claim 9, wherein the thioglycolic ester is glycerol monothioglycollate.

11. Agent according to claim 9, said agent comprising a mixture of (a) a thioglycolic acid ester; (b) from 20 to 30% of said thioglycolic acid ester of a combination of 2-mercaptopropionic acid monoglycerol ester and 3-mercaptopropionic acid monoglycerol ester; and (c) at least one solubilizer.

12. Agent according to claim 11, wherein the thioglycolic ester is glycerol monothioglycollate.

* * * * *